(12) United States Patent
Hannula

(10) Patent No.: US 6,584,344 B2
(45) Date of Patent: Jun. 24, 2003

(54) METHOD AND APPARATUS FOR MEASURING HEART RATE

(75) Inventor: Manne Hannula, Oulu (FI)

(73) Assignee: Polar Electro Oy, Kempele (FI)

( * ) Notice: Subject to any disclaimer, the term of this patent is extended or adjusted under 35 U.S.C. 154(b) by 333 days.

(21) Appl. No.: 09/790,279

(22) Filed: Feb. 22, 2001

(65) Prior Publication Data

US 2002/0115938 A1 Aug. 22, 2002

(51) Int. Cl.⁷ .............................................. A61B 5/04
(52) U.S. Cl. ..................... 600/509; 600/519; 600/520; 600/521
(58) Field of Search ................. 600/503, 508, 600/509, 519, 520, 521; 128/903, 905

(56) References Cited

U.S. PATENT DOCUMENTS

| | | | |
|---|---|---|---|
| 4,248,244 A | | 2/1981 | Charnitski et al. .......... 600/519 |
| 4,295,472 A | * | 10/1981 | Adams ....................... 600/519 |
| 4,325,384 A | * | 4/1982 | Blaser et al. ................ 600/509 |
| 4,420,000 A | | 12/1983 | Bailey ........................ 600/519 |
| 4,478,224 A | | 10/1984 | Bailey ........................ 600/519 |
| 4,938,228 A | * | 7/1990 | Righter et al. .............. 600/519 |
| 5,394,879 A | * | 3/1995 | Gorman ...................... 600/520 |
| 5,738,104 A | | 4/1998 | Lo et al. ..................... 600/521 |
| 5,820,567 A | * | 10/1998 | Mackie ....................... 600/519 |
| 5,876,350 A | | 3/1999 | Lo et al. ..................... 600/519 |
| 6,018,677 A | * | 1/2000 | Vidrine et al. .............. 600/520 |
| 6,163,718 A | * | 12/2000 | Fabrizio ...................... 600/519 |
| 6,304,774 B1 | * | 10/2001 | Gorman ...................... 600/520 |
| 6,405,077 B1 | * | 6/2002 | Birnbaum et al. .......... 600/520 |

* cited by examiner

Primary Examiner—Willis R. Wolfe
(74) Attorney, Agent, or Firm—Hoffmann & Baron, LLP

(57) ABSTRACT

An arrangement for detecting a heart beat and calculating heart rate on the basis of the detected heart beats, comprising means for measuring an EKG signal from a person's hands, a computer for detecting a heart beat from the measured signal and for performing a rationality analysis to verify a heart beat detection and for calculating the heart rate on the basis of the detected heart beats, the arrangement further comprising means for displaying the calculated heart rate and connected to the computer.

22 Claims, 5 Drawing Sheets

METHOD AND APPARATUS FOR MEASURING HEART RATE

FIELD OF THE INVENTION

The field of application of the invention is the measurement of heart rate frequency, i.e. pulse, and especially the calculation of heart rate on the basis of an EKG signal measured from hands.

BACKGROUND OF THE INVENTION

A heart rate monitor is an apparatus used in sports and medicine, by means of which it is possible to monitor the functions of the heart, such as heart rate, standard deviation of heartbeat intervals, or other corresponding heart rate information derived from the functioning of the heart. There are two types of heart rate monitors which differ from each other in principle. Heart rate monitors of the first type measure heart rate frequency optically from the flow of blood in blood vessels or heart rate as pressure measurement from blood vessels. Typically, optical measurement and pressure measurement are done from hands, from wrist, for instance. Heart rate monitors based on the measurement of an EKG signal are in the second category of heart rate monitors. The EKG signal is strongest on the chest of a person where the most reliable measuring results are obtained, but especially in sports applications, areas providing weaker electric signals, such as wrists and palms, are used in signal measurement for reasons of comfort and practicability.

Many kinds of solutions for heart rate monitors are known. A structure based on a heart rate transmitter belt located on the chest and a wrist receiver can be mentioned as an example. Further, some heart rate monitor solutions are implemented solely by a wrist apparatus, in which case the heart rate measurement and processing occur in one unit. Instead of these portable heart rate monitor solutions, heart rate measurement functions can also be integrated in sports apparatuses, such as exercise bikes, steppers and treadmills. In these apparatuses, heart rate measuring sensors are located in the handles, i.e. heart rate is measured on the basis of an EKG signal measured from palms.

One of the most difficult heart rate measuring arrangements is measuring the EKG by means of measuring electrodes placed in the handles of an exercise apparatus. The measuring environment in question is especially difficult because unlike in the case of a wrist apparatus or heart rate transmitter belt, the measuring electrodes are not attached to the body. The movement of hands in relation to the handles and the electrodes located on them causes interference to the signal being measured, as does the EMG signal caused by the movement of muscles.

U.S. Pat. No. 5,738,104 discloses a prior art solution for EKG signal measurement and heart rate formation on the basis of the measured signal. The solution disclosed in the publication measures the EKG signal by means of at least three measuring electrodes and tries to locate an R peak of the QRS complex from the measured signal. U.S. Pat. No. 5,876,350 describes another prior art solution for calculating heart rate frequency on the basis of an EKG signal.

Prior art solutions may produce satisfactory results in good measuring conditions, but they do not, however, provide conditions for a successful heart beat detection in an environment comprising interference, such as in a measurement done from the handles of an exercise apparatus. During a fitness exercise, the EMG signal caused by the movement of muscles and the movement of hands in relation to the handles cause interference to the measuring signal, and the elimination of this interference appears insufficient on the basis of the solutions disclosed in the reference publications. Due to their inaccuracy, the solutions easily lead to incorrect detection, and consequently, the calculation of heart rate loses its reliability.

It is thus clear that there is a need to develop a method and an apparatus so as to achieve a sufficiently reliable heart beat detection and heart rate calculation in a measuring situation comprising a great deal of interference.

BRIEF DESCRIPTION OF THE INVENTION

It is an object of the invention to provide an improved solution for measuring heart rate from hands. This is achieved by the following method for detecting a heart beat and calculating heart rate on the basis of the detected heart beats, the method comprising forming an EKG signal on the basis of signals measured from the skin of a person, detecting from the EKG signal a heart beat candidate to which a rationality analysis is performed, in which the time difference between the heart beat candidate and the heart beat detection preceding it is calculated and on the basis of the time difference, a momentary heart rate value is calculated, the calculated momentary heart rate value is compared with a median value of the heart rate, which is a median of two or more earlier heart rate values, the heart beat candidate is accepted as a heart beat detection, if the momentary heart rate value calculated on the basis of the heart beat candidate is, when compared with the median value, within threshold values of the median value, and updating as the heart rate value the momentary heart rate value calculated on the basis of the accepted heart beat detection.

The invention also relates to an arrangement for detecting a heart beat and calculating heart rate on the basis of the detected heart beats, comprising at least one measuring electrode for measuring a signal from the skin of one hand of a person, and at least one measuring electrode for measuring a signal from the skin of the other hand, an amplifier connected to said measuring electrodes for amplifying the potential difference of the signals measured by the measuring electrodes to form an EKG signal, an analog-to-digital converter for receiving the signal from the amplifier and for converting the signal into digital format to be a sample signal containing samples, and a computer which is arranged to read the digital signal and to detect from the sample signal a heart beat candidate, to perform a rationality analysis to the heart beat detection, in which the computer is arranged to calculate a time difference between the heart beat candidate and the heart beat detection preceding it, and to calculate a momentary heart rate value on the basis of the time difference, to compare the calculated momentary heart rate value with a median value of the heart rate, which is a median of two or more earlier calculated heart rate values, to accept the heart beat candidate as the heart beat detection, if the momentary heart rate value calculated on the basis of the heart beat candidate is, when compared with the median value, within threshold values of the median value, and to update as the heart rate value the momentary heart rate value calculated on the basis of the accepted heart beat detection, the arrangement further comprising display means connected to the computer and displaying the heart rate value calculated on the basis of the accepted heart beat detections.

Preferred embodiments of the invention are set forth in the dependent claims.

The invention thus relates to a method and an apparatus for detecting a heart beat from an EKG signal and calculating heart rate on the basis of the detected heart beats. In the solution of the invention, the measurement of the heart rate signal is preferably done from hands, as in the measurement from the handles of an exercise apparatus, in which the measurement is done from the skin of a palm or finger tip, for instance. Detecting the signal is considerably easier when measured from the chest than elsewhere on the body, which means that the problems related to the measurement are then completely different from measurement in a measuring area where the ratio of the interfering signal to the measuring signal is high. The calculated heart rate is displayed to the user by the display means of the exercise apparatus, such as a liquid crystal display.

In the solution of the invention, a heart beat candidate is searched from an EKG signal, and a rationality analysis is performed to it. In the analysis, it is checked that the heart beat detection is in temporal proportion to previous accepted detections in such a manner that the heart beat candidate can be accepted as a heart beat detection to be used in calculating heart rate. In examining accepted heart beat detections, a preferably short time-window, for instance three seconds, is used. A median value is calculated for the heart rate on the basis of the heart beat detections in the time window. Using a median provides the advantage that unnecessarily high or low values in the time intervals of the examination point, which may be related to incorrect detections, will not be taken into account in the calculation, contrary to a calculation which uses an average, for instance. The heart beat candidate is accepted as a heart beat detection, if the heart rate calculated on the basis of the candidate differs upwards or downwards from the median less than the threshold values, i.e. for instance 10 beats a minute. Otherwise, the tentative heart beat candidate is rejected as an incorrect detection. The background for median calculation is that the alteration rate of heart rate, whether increasing or decreasing, is limited by the human body and can be relatively accurately defined. Heart rate calculation is preferably done at least at two-second intervals.

In a preferred embodiment of the method of the invention, an electric signal is measured from a person's skin at two measuring points, and a potential difference between the measured signals is formed by means of a differential amplifier. Signal processing operations are performed to the formed signal, such as analog filtering in which frequencies outside the frequency range of 5 to 40 Hz are filtered from the signal. The obtained measuring signal is converted into digital format to be a sample signal which is examined during the heart beat search process. In heart beat detection, a sample window is slid over sample signals, i.e. the sample signal being examined is read from the memory buffer or in real-time to the sample window, and from the other end of the sample window, the sample signal moves away from processing. The sample signal in the sample window is read one sample at a time until a local maximum value is detected in the sample signal. A local maximum is required to exceed a threshold value which is set in advance or modifiable according to existing conditions. A threshold value can be formed in an existing measuring situation to be, for instance, twice the average interference power. After finding the local maximum, the routine checks if a local minimum which is lower than a threshold value set for the local minimum, follows the local maximum. Further, a local maximum which exceeds a threshold value set for a second local maximum, must follow the local minimum.

A preferred embodiment of the invention examines the time difference of the above-mentioned local minimum to the first local maximum and the second local maximum or to at least one of them. If the time difference is within the threshold values set for the time difference, the detected heart beat can be tentatively accepted.

The method and apparatus of the invention provide the advantage that heart rate can be calculated considerably more reliably in an environment comprising interference. The apparatus implementing the method is simpler, faster and less expensive in structure than the prior art solutions.

BRIEF DESCRIPTION OF THE FIGURES

In the following, the invention will be described in greater detail with reference to the accompanying drawings in which.

DETAILED DESCRIPTION OF THE EMBODIMENTS

Figure 1:
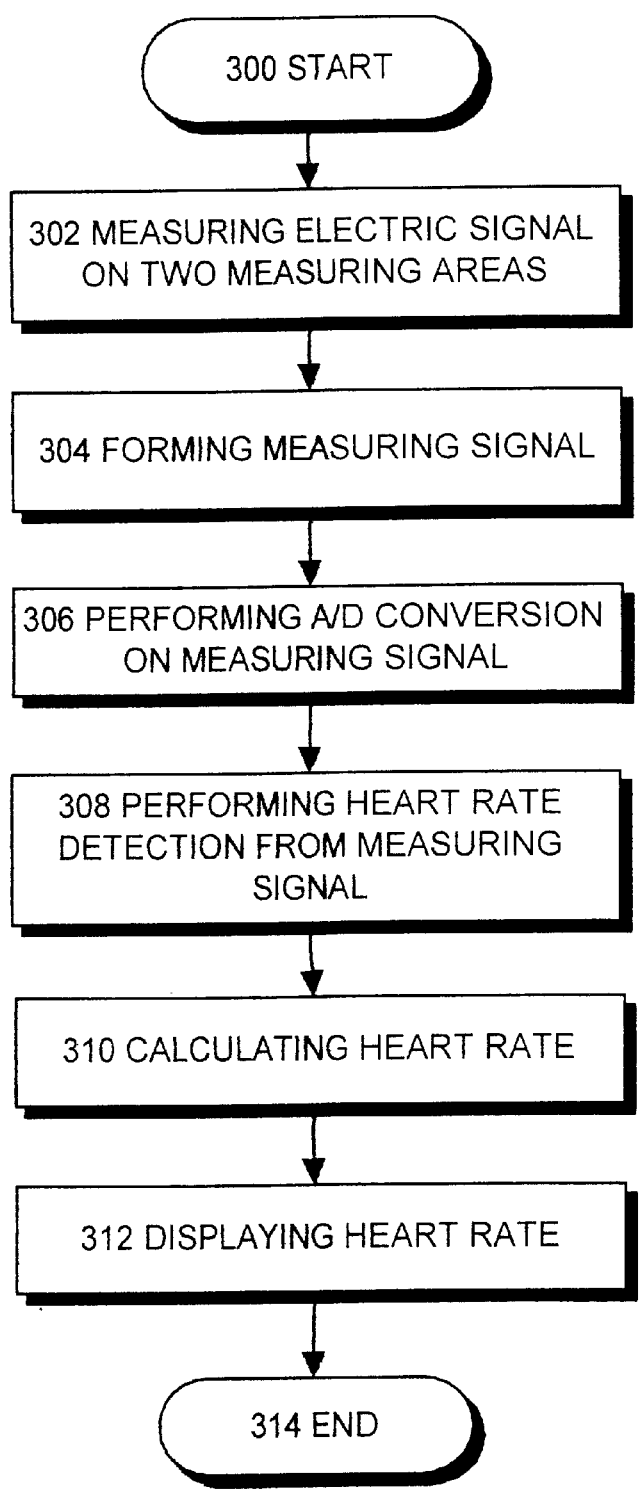
FIG. 1 shows a preferred embodiment of the method of the invention.
Figure 3:
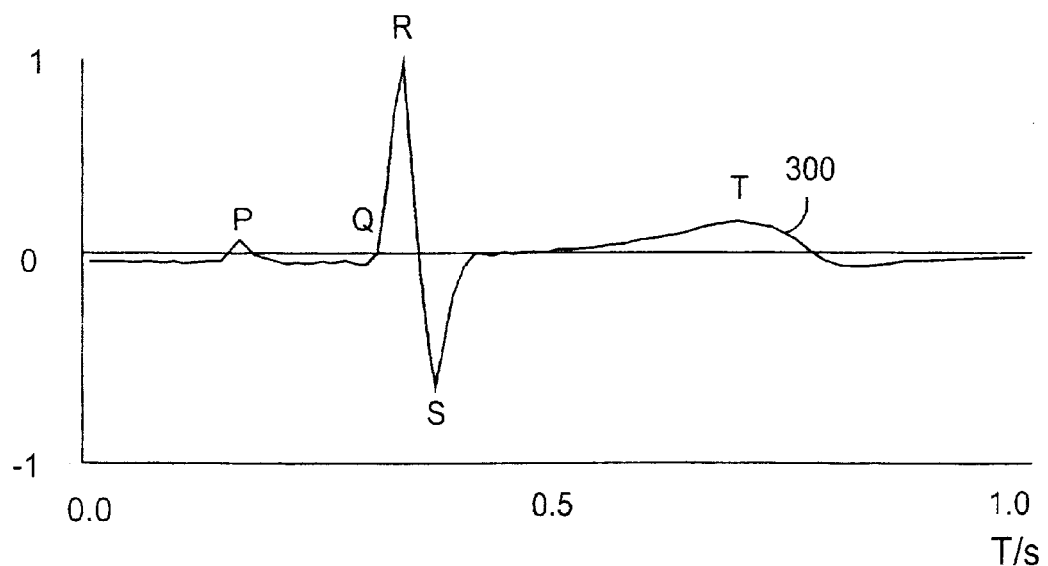
FIG. 3 shows an electric signal caused by electric activation of the heart.

In the following, the invention will be described with reference to the accompanying drawings describing preferred embodiments. One preferred embodiment of the method of the invention is described in FIG. 1. The starting step 300 of the method refers to a situation in which heart rate measurement from a user is being started during a fitness exercise, for instance. The measuring is performed continuously during the exercise on at least two measuring locations on the user, shown as method step 302. The areas being measured are preferably located on different sides of the electric activation vector caused by a heart beat. The activation vector determines the strength of the EKG signal on a person's skin in such a manner that the maximum value is reached at the starting point of the vector on the right shoulder and the minimum point at the end point of the vector on the left heel. In a preferred embodiment, the signal is measured from both hands, for instance from palms or fingertips. An EKG signal 300 is obtained as the potential difference of the measured signals and its form is presented as a function of time in FIG. 3. The amplitude of a typical EKG signal is 1 to 2 mV measured with a good electrode contact from the chest, but if the skin is dry, it can be as low as 200 $\mu$V. A signal measured from a finger or hand is a great deal weaker than this. The most reliable heart rate measurement is obtained by QRS-complex detection from an EKG signal, because it contains the most energy and its spectrum differs sufficiently from the spectrum of movement artefacts. When heart rate increases due to strain, the duration and amplitude of the EKG signal properties remain almost unchanged in a healthy person and only the distance from a P wave to the next P wave becomes shorter. The EKG spectrum contains the most significant frequency components from 2 Hz to approximately 20 to 30 Hz. The QRS complex peak, i.e. the R peak, is in the frequency range of 10 to 15 Hz. In FIG. 3, the signal is scaled so that the most significant R peak is scaled to the value 1 and the other peaks in relation to it. Most disturbances in measuring heart rate are caused by movement artefacts, and to minimize these disturbances, the electrode contact must be good and the electrode material correctly selected. The spectrum of P and T waves and the spectrum of movement artefacts is in the frequency range of 1 to 5 Hz, which is below the frequency range of the QRS complex and therefore easy to filter away. EMG interference can also be significantly reduced by moving the electrodes away from large muscles, which do not exist in hands, for instance. Interference caused by an electric network (in the frequency range of 50/60 Hz) does not exit outdoors elsewhere than in the immediate vicinity of high-voltage lines. Indoors, network interference may disturb measurement for instance in hospitals and gyms. This interference can be reduced with a band-stop filter without attenuating the frequency components of the actual EKG signal.

In method step 304, the EKG signal is led to the computer for processing. Analog filtering is also performed on the signal to filter away said desired frequency components. In method step 306, the filtered analog signal is A/D-converted to form a digital signal. In method step 308, heart beat detection is performed to the obtained digital signal, i.e. the routine tries to locate heart beats temporally and to obtain sufficient sureness that they are heart beats and not interference caused to the signal by the environment or body movements. Heart beat detection is described in greater detail in connection with FIG. 2. In method step 310, the heart rate of a person is calculated on the basis of the heart beats detected in step 308. Statistics are kept of the detected heart beats on the computer for the operating situation in question. The statistics preferably maintain time intervals between detections from the beginning of the exercise, and time intervals between detections for the past minute, for instance, when such information is available, and for approximately the past two seconds for the purpose of calculating the heart rate. The calculated heart rate is displayed to the user by the display means of the heart rate monitor. The display means comprise a heart rate monitor display or a sound signal. Heart rate information can also be stored in the memory of the heart rate monitor and displayed by an external computer connected later to the heart rate monitor. It is clear that the method steps 302 to 310 described above are continuous processes and performed parallel during the signal measurement.

Figure 2:
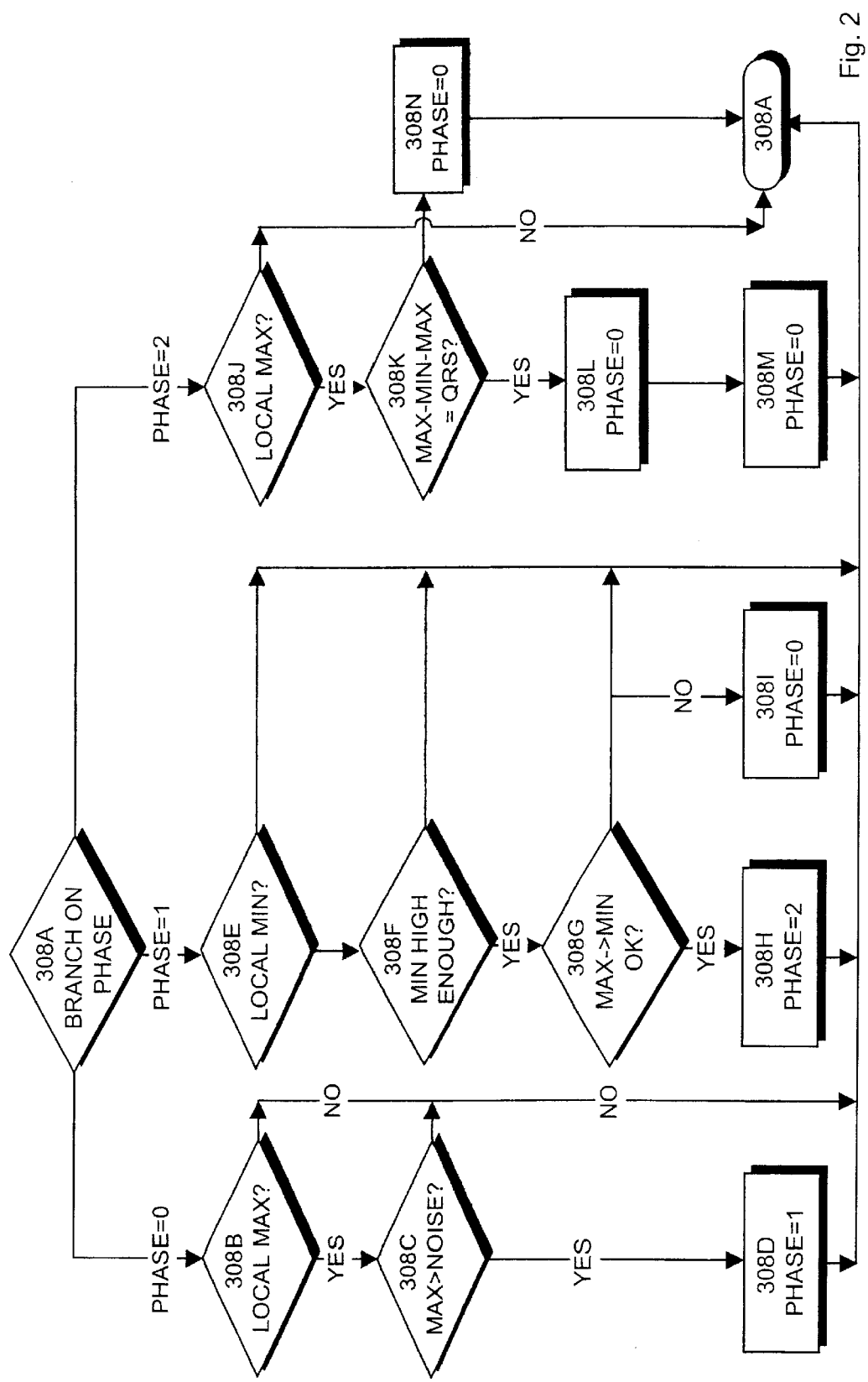
FIG. 2 shows a preferred embodiment for detecting a heart beat according to a preferred embodiment of the method of the invention.

FIG. 2 shows the detection of a heart beat using an embodiment. FIG. 2 expands on method steps 308 and 310 shown in FIG. 1. Selection node 308A receives a signal in such a manner that a sample window of desired length, for instance 1200 ms, is moved over the sampled signal. During phase 0 (phase=0), selection node 308B searches for a local maximum value from the signal. In a local maximum, the values of the signal samples preceding and following a signal sample must be smaller than the value of the signal sample being examined. If the sample was not a local maximum, the routine returns to branch node 308A, otherwise the routine checks in condition node 308C that the value is higher than the value corresponding to noise. A threshold value, for instance 40% of the R peak amplitude, has been set to noise in advance. If the signal peak exceeds the noise threshold value, the routine continues to phase 1 (phase=1), otherwise it returns to branch node 308A. From the branch node, the routine moves to phase 1, if a local maximum has been located. Condition node 308E examines whether a sample fulfills the characteristics of a local minimum, i.e. the sample preceding and following said sample must correspond to higher signal amplitude values than the sample being examined, and that the local minimum is sufficiently low, being lower than a threshold value set to it. If the sample was not a local minimum, the routine returns to node 308A to receive the next sample. The signal is examined one sample at a time until the condition for a local minimum is fulfilled and it is possible to move to condition node 308F to check if the amplitude of the minimum value is high enough. If this is not the case, the routine returns to node 308A, otherwise it continues to condition node 308G to check if the temporal distance between the maximum and the minimum is within threshold values surrounding the expected value. In this case, the expected value refers to a reference value obtained on the basis of a few first detections or a value defined on the basis of a heart rate recording made in advance on the user. Threshold values can be set so, for instance, that their ratio to the expected value is ±10%. If the condition in node 308G is fulfilled, heart beat detection proceeds to phase 2, otherwise it is noted that the maximum found in step 308B and the minimum accepted in step 308F do not fulfill the characteristics of a heart beat. If the time limit allows to continue searching for a local minimum;, the routine continues with the next sample in step 308A. Otherwise it is noted that the local maximum was caused by an incorrect detection or the local minimum was lost in signal interference, and the phase is again set to 0 and the analysis of the samples is started again from the beginning by searching for a local maximum.

Phase 2 examines in condition node 308J whether the sample fulfills the characteristics set to a second local maximum. If this is not the case, the routine returns to step 308A to read the next sample. If a second local maximum was found, the routine checks in condition node 308K the applicability of the three found peaks max-min-max to the shape of the QRS complex. The peaks are checked to see for instance that the temporal distances of the second local maximum to the first local maximum and minimum are within allowed limits.

The detection of a heart beat candidate was performed in the above solution according to the method steps of FIG. 2. A rationality analysis will then be performed to the heart beat candidate, i.e. the routine checks that the time instant of the heart beat detection is rational in relation to previous accepted heart beat detections. For instance, if the difference between the heart beat candidate and the previous accepted heart beat detection is 0.500 seconds, the momentary heart rate is then 120. The rationality analysis preferably examines heart rate values backwards from the examination time using an approximately three-second window. A median is calculated from the stored heart rate values thus calculated, and the new heart rate value is compared with it. For instance, if for the past two seconds, there are three detection differences, 0.605 s, 0.635 s and 0.615 s, in the memory, 0.615 s is used as the median value. If the time difference between the heart beat candidate and the previous accepted detection is 0.595 seconds, the heart rates formed from them are compared with each other. If the new heart rate frequency value differs too much from the median, the new heart rate value is not accepted. It can be required, for instance, that the heart rate not differ over 10 beats/minute from the previous heart rate value before accepting the calculated heart rate value. In said example, 0.615 seconds produces a heart rate of 98, whereas 0.595 seconds produces a heart rate of 101, i.e. the new heart rate value is acceptable. This rationality examination is based on the physiological properties of man, i.e. to the fact that the alteration rate of heart rate is limited in both increasing and decreasing direction. In a preferred embodiment, the heart beat candidate in a time window is not accepted immediately if it fulfills the conditions described above, but the routine waits for a certain time and then checks if more heart beat candidates can be found in the time window. In such a case, the heart beat detection is preferably selected which provides the heart rate value closest to the valid heart rate value. Alternatively, the heart beat candidate is selected which provides the heart rate value closest to the heart rate median.

Figure 4A:
FIG. 4 shows a preferred embodiment of the detection principle of heart beat detection and the use of consecutive heart beat time-intervals in heart rate calculation.
Figure 4B:
Figure 4C:
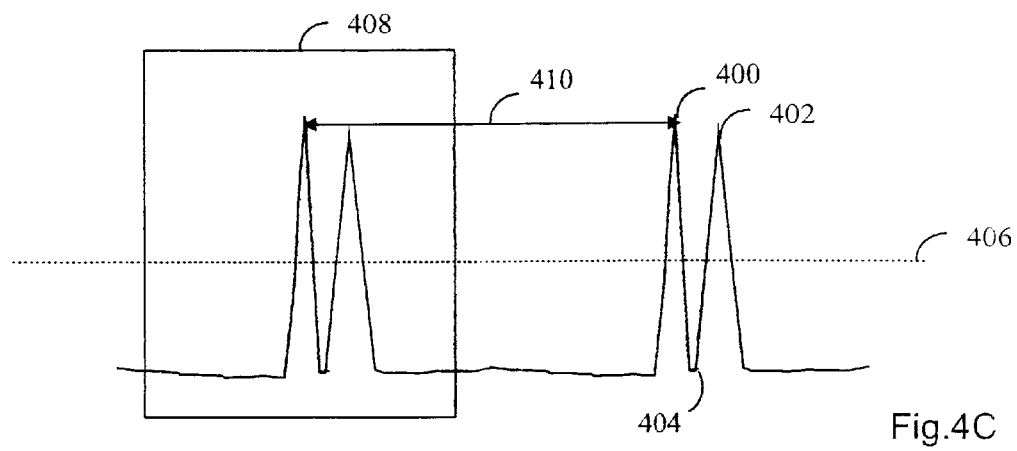

FIG. 4A shows by way of example an analog-filtered signal, from which signal components corresponding to movement artefacts and frequency components exceeding the frequency band of the EKG signal have been filtered. Filtering alters the shape of the signal from the original EKG signal shape. The information content of the signal is, however, sufficient to identify the R peak, and the signal-to-noise ratio can thus be improved. After filtering, the signal is differentiated to enhance the signal processing of the following phases. FIG. 4B shows a signal amplified by differentiation, which again shows a typical up-down wave shape. To facilitate the examination of the signal, the absolute value of the signal shown in FIG. 4C is obtained, in which negative peaks have been converted into positive. The signal shown in FIG. 4C can further be thought to be A/D-converted, in which case the points of the signal 300 shown in the figure represent the digital values of the signal samples as a function of time. The high point 400 corresponding to the R peak of the EKG signal is the first local maximum found in phase 0 of method FIG. 2. The local maximum is required to exceed the threshold value 406. The threshold value can, for instance, be set to 50% of the R peak amplitude. An average of ten previous heart beat detection R peaks can be used in the calculation, for instance. One preferred embodiment measures the average of noise during a certain time, and sets the threshold value at 150% with respect to the average of noise. The minimum point 404 of the signal refers to the local minimum found in phase 1 of FIG. 2. The local minimum must be lower than the threshold value corresponding to the minimum. The same threshold value as in the case of the first local maximum can naturally be used, or a different threshold value selected. The peak corresponding to the second peak of the EKG signal is marked in FIG. 4C by the second local maximum 402. The second local maximum 402 is accepted in the same manner as the first local maximum 400 and the local minimum 404. One preferred embodiment uses the same threshold value as the threshold value 406 of the first and second local maximum.

Not only threshold values are used in accepting a heart beat detection, but also rationality analyses which were preliminarily referred to in connection with the description of the method FIG. 2. The found points 400 (local maximum) and 404 (local minimum) are examined to see that the time difference between them is within the threshold values set to the difference. The threshold values set to the difference can be formed in such a manner, for instance, that an average of the time differences of the detected heart beats are calculated, and a time difference of ±20% to the average is set as the acceptance criterion. A corresponding acceptance procedure is also performed in a preferred embodiment on the distance between the minimum point and the second local maximum. The time difference between a first and second peak is preferably also checked and a corresponding acceptance procedure based on threshold values is applied. In a preferred embodiment, the signal peaks 400 and/or 402 are set amplitude limits instead of a lower threshold value only, and the value of the sample must be within the digital values corresponding to the amplitude limits before acceptance. FIG. 4C shows a sample window 408 which is moved one sample at a time to the right in the figure, i.e. the heart rate signal 300 moves to the left in the figure. The temporal distance between two R peaks, i.e. two heart beats, is marked by line segment 410. According to the description of FIG. 2, the time differences of heart beats are stored into memory during a certain time, and said time differences are used in connection with the heart rate calculation to make rationality estimates. At this time, there is a need to make sure that the heart rate does not change too quickly during the calculation interval of the heart rate, which is for instance three seconds.

Figure 5:
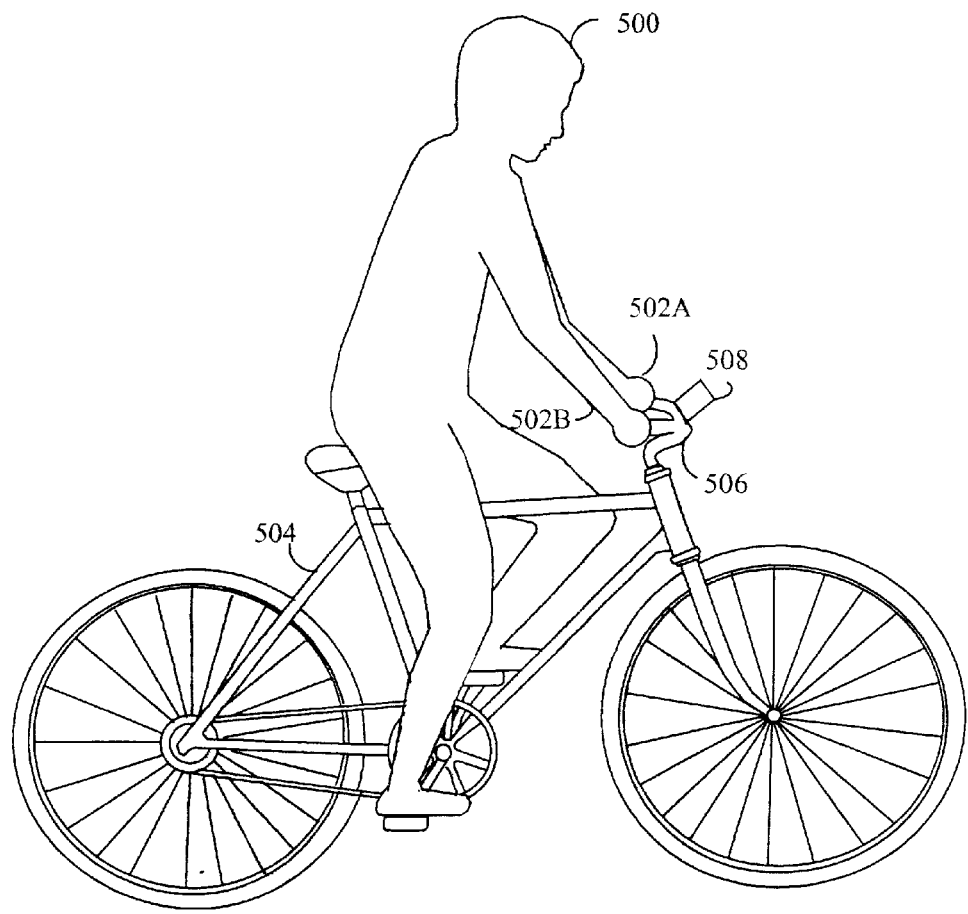
FIG. 5 shows an application of the apparatus of the invention.

FIG. 5 shows an apparatus according to a preferred embodiment. The figure shows a person 500 pedaling a bicycle 504, whose heart rate needs to be measured. The hands 502A and 502B of the person 500 are on the handlebar 506 of the bicycle 504, and electrodes measuring the electric signal caused by heart beat from hands are located in the handles of the handlebar. A display 508 for displaying the heart rate is also connected to the handlebar 506 of the bicycle 504. The presented solution is not only suitable for bicycles, but also for exercise bikes, steppers, treadmills, rowing machines or the like, in which hands are held on handles so that the skin of the hand is in immediate contact with the handles.

Figure 6:
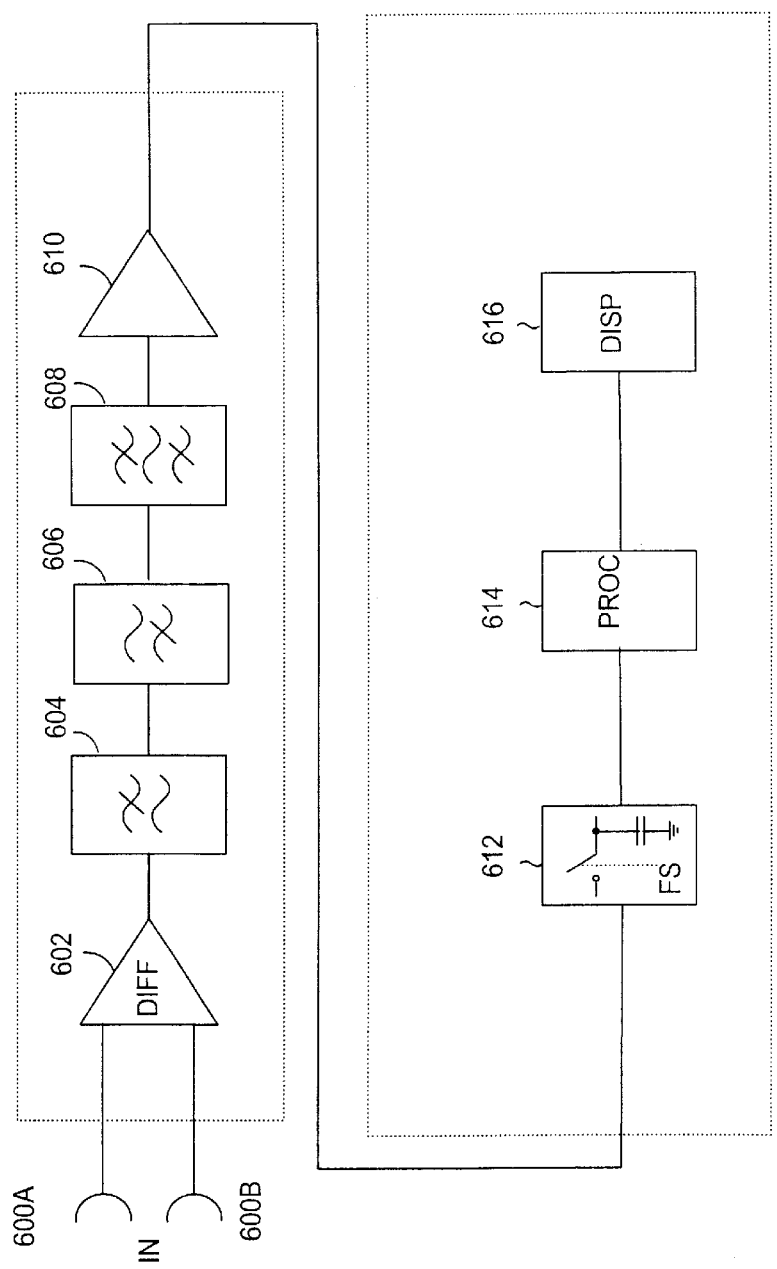
FIG. 6 shows a preferred embodiment of the apparatus of the invention.

FIG. 6 shows a preferred embodiment of the arrangement of the invention. The signal is measured from a person's hands by two measuring electrodes 600A and 600B. The electrodes being used are resistive or capacitive sensors according to prior art; due to the environment comprising interference, preferably capacitive sensors. The analog electronics of the arrangement contain blocks 620 to 610 and the digital electronics blocks 614 to 620. A differential amplifier 602 receiving inlet signals amplifies all frequencies of a signal by 40 dB, for instance. This way, the 50 to 60 Hz interference induced to the person from surrounding electric wires and devices is amplified in proportion to the EKG signal being measured. Eliminating the network interference in question as well as the low-frequency EMG interference is done by a low-pass filter 604, high-pass filter 606 and band-stop filter 606. Filtering also attenuates the desired EKG signal which is amplified by an amplifier 608.

An A/D converter 612 converts the analog signal to digital format. The sampling frequency is for instance 500 Hz (2 ms), which means that the arrangement can at most sample a signal having a highest frequency of 250 Hz (4 ms). The signal samples are analyzed in a general purpose processor 614 in which the steps of the method are preferably implemented by program. The steps of the method can also be implemented by ASIC or using separate logic components. The processor is connected to heart rate display means 616. The display means can be implemented using a liquid crystal display, for instance. Alternatively, the display can be done using an external apparatus, such as a computer, in which case the arrangement comprises telecommunications means for the arrangement to communicate with the external computer. It is clear that the arrangement for measuring, processing and displaying heart rate also comprises other parts, but their presentation is not essential for the invention.

Even though the invention has been explained in the above with reference to examples in accordance with the accompanying drawings, it is obvious that the invention is not restricted to them but can be modified in many ways within the scope of the inventive idea disclosed in the attached claims.

What is claimed is:

1. A method for detecting a heart beat and calculating heart rate on the basis of the detected heart beats, the method comprising:
   forming an EKG signal on the basis of signals measured from the skin of a person,
   detecting from the EKG signal a heart beat candidate to which a rationality analysis is performed, in which rationality analysis:
      the time difference between the heart beat candidate and the heart beat detection preceding it is calculated and on the basis of the time difference, a momentary heart rate value is calculated,
      the calculated momentary heart rate value is compared with a median value of the heart rate, which is a median of two or more earlier heart rate values,
      the heart beat candidate is accepted as a heart beat detection, if the momentary heart rate value calculated on the basis of the heart beat candidate is, when compared with the median value, within threshold values of the median value, and
      updating as the heart rate value the momentary heart rate value calculated on the basis of the accepted heart beat detection.

2. A method as claimed in claim 1 wherein the EKG signal is analyzed in the rationality analysis using an approximately three-second time window, and the median value of the heart rate is calculated on the basis of the accepted heart beat detections in the time window.

3. A method as claimed in claim 1, wherein the EKG signal is analyzed in the rationality analysis using a time window, and if there are more than one heart beat candidate in the time window, the heart beat candidate is selected as the heart beat detection, the heart rate value calculated from which is closest to the valid heart rate value.

4. A method as claimed in claim 1, wherein the EKG signal is analyzed in the rationality analysis using a time window, and if there are more than one heart beat candidate in the time window, the heart beat candidate is selected as the heart beat detection, the heart rate value calculated from which is closest to the median value of the heart rate.

5. A method as claimed in claim 1, wherein the EKG signal is analyzed in the rationality analysis using a time window, and the median value of the heart rate is calculated on the basis of the accepted heart beat detections in the time window, and approximately ten beats a minute is used as the threshold value of the median.

6. A method as claimed in claim 1, wherein an EKG signal is measured from a person's hands in an exercise apparatus having handles, in which a measuring electrode is located in both handles of the exercise apparatus for setting against the skin of the person's hand for the purpose of measuring the EKG signal.

7. A method as claimed in claim 1, wherein
   a signal is measured from a person's skin at a minimum of two measuring points, and an analog EKG signal is formed by means of the potential difference of said signals,
   the EKG signal is converted into digital format to be a sample signal containing samples,
   the sample signal is read one sample at a time until a first sample can be located from the sample signal, which exceeds a threshold value set to a first maximum value of the EKG signal and contains a local maximum, and until a second sample can be located from the sample signal, which is lower than a minimum value of the EKG signal and contains a local minimum, and until a third sample can be located from the sample signal, which exceeds a threshold value set to a second maximum value of the EKG signal and contains a second local maximum,
   the part of the sample signal formed by the first, second and third sample is accepted as the heart beat candidate.

8. A method as claimed in claim 7, wherein a threshold value is used for the first maximum value, which is approximately 50% of the average R peak amplitude of the earlier accepted heart beat detections of the person.

9. A method as claimed in claim 7, wherein the average noise level is calculated during the measurement of the EKG signal, and a threshold value is used for the first maximum value, which is approximately 150% with respect to the average of noise.

10. A method as claimed in claim 7, wherein the same threshold value is used for the minimum value and the second maximum value as for the first maximum value.

11. A method as claimed in claim 7, wherein the time difference between the first sample and the second sample is calculated, and a part of the sample signal is accepted as a heart beat only if the time difference is within the limits defined by the threshold values set for the time difference.

12. An arrangement for detecting a heart beat and calculating heart rate on the basis of the detected heart beats, comprising:
   at least one measuring electrode for measuring a signal from the skin of one hand of a person, and at least one measuring electrode for measuring a signal from the skin of the other hand,
   an amplifier connected to said measuring electrodes for amplifying the potential difference of the signals measured by the measuring electrodes for the purpose of forming an EKG signal,
   an analog-to-digital converter for receiving the signal from the amplifier and for converting the signal into digital format to be a sample signal containing samples, and
   a computer which is arranged:
      to read the digital signal and to detect from the sample signal a heart beat candidate,
      to perform a rationality analysis for the heart beat detection, in which the computer is arranged:
         to calculate a time difference between the heart beat candidate and the heart beat detection preceding it, and to calculate on the basis of the time difference, a momentary heart rate value,
         to compare the calculated momentary heart rate value with a median value of the heart rate, which is a median of two or more earlier calculated heart rate values,
         to accept the heart beat candidate as a heart beat detection, if the momentary heart rate value calculated on the basis of the heart beat candidate is, when compared with the median value, within threshold values of the median value, and
         to update as the heart rate value the momentary heart rate value calculated on the basis of the accepted heart beat detection,
      the arrangement further comprising display means connected to the computer and displaying the calculated heart rate value on the basis of the accepted heart beat detections.

13. An arrangement as claimed in claim 12, wherein the computer is arranged to analyze the EKG signal in the rationality analysis using an approximately two-second time window, and to calculate the median value of the heart rate on the basis of the accepted heart beat detections in the time window.

14. An arrangement as claimed in claim 12, wherein the computer is arranged to analyze the EKG signal in the rationality analysis using a time window, and if there are more than one heart beat candidate in the time window, to select as the heart beat detection the heart beat candidate, the heart rate value calculated from which is closest to the valid heart rate value.

15. An arrangement as claimed in claim 12, wherein the computer is arranged to analyze the EKG signal in the rationality analysis using a time window, and if there are more than one heart beat candidate in the time window, to select as the heart beat detection the heart beat candidate, the heart rate value calculated from which is closest to the median of the heart rate.

16. An arrangement as claimed in claim 12, wherein the computer is arranged to analyze the EKG signal in the rationality analysis using a time window, and to calculate the median value of the heart rate on the basis of the accepted heart beat detections in the time window, and to use approximately ten beats a minute as the threshold value of the median.

17. An arrangement as claimed in claim 12, wherein the arrangement is an exercise apparatus comprising handles for supporting the hands during exercise, and measuring electrodes are placed in the handles of the exercise apparatus so that both handles have at least one measuring electrode for setting against the skin of the person's hand for the purpose of measuring the EKG signal.

18. An arrangement as claimed in claim 12, wherein the computer is arranged to read the sample signal one sample at a time until a first sample can be located from the sample signal, which exceeds a threshold value set to a first maximum value of the EKG signal and contains a local maximum, and until a second sample can be located from the sample signal, which is lower than a minimum value of the EKG signal and contains a local minimum, and until a third sample can be located from the sample signal, which exceeds a threshold value set to a second maximum value of the EKG signal and contains a second local maximum, and to accept the part of the sample signal formed by the first, second and third sample as the heart beat candidate.

19. An arrangement as claimed in claim 18, wherein the computer is arranged to use for the first maximum value a threshold value which is approximately 50% of the average R peak amplitude of the earlier accepted heart beat detections of the person.

20. An arrangement as claimed in claim 18, wherein the computer is arranged to calculate the average noise level during the measurement of the EKG signal, and to use for the first maximum value a threshold value which is approximately 150% with respect to the average of noise.

21. An arrangement as claimed in claim 18, wherein the computer is arranged to use the same threshold value for the minimum value and the second maximum value as for the first maximum value.

22. An arrangement as claimed in claim 18, wherein the computer is arranged to calculate the time difference between the first sample and the second sample, and to accept a part of the sample signal as a heart beat detection only if the time difference is within the limits defined by the threshold values set for the time difference.

* * * * *